United States Patent

Mueller et al.

[11] Patent Number: 6,086,366
[45] Date of Patent: Jul. 11, 2000

[54] DEVICE FOR REMOVING MATERIAL FROM A WORKPIECE BY LASER RADIATION

[75] Inventors: Gerhard Mueller, Berlin; Thomas Ertl, Mahlow; Hartmut Benthin, Berlin, all of Germany

[73] Assignee: Clinicon Corporation, Carlsbad, Calif.

[21] Appl. No.: 09/029,966

[22] PCT Filed: Sep. 11, 1996

[86] PCT No.: PCT/DE96/01788

§ 371 Date: Jun. 11, 1998

§ 102(e) Date: Jun. 11, 1998

[87] PCT Pub. No.: WO97/12559

PCT Pub. Date: Apr. 10, 1997

[30] Foreign Application Priority Data

Sep. 11, 1995 [DE] Germany .............. 195 34 590

[51] Int. Cl.[7] .................................. A61C 1/00
[52] U.S. Cl. .................. 433/29; 606/2; 606/12
[58] Field of Search .............. 433/29, 215; 606/2, 606/11, 12, 13, 14, 15, 16, 17

[56] References Cited

U.S. PATENT DOCUMENTS

| | | | |
|---|---|---|---|
| 4,622,971 | 11/1986 | Yamamoto et al. | 606/2 |
| 4,761,054 | 8/1988 | Ishimori et al. | 350/96.26 |
| 5,020,995 | 6/1991 | Levy | 433/215 |
| 5,364,390 | 11/1994 | Taboada et al. | 433/215 |
| 5,415,652 | 5/1995 | Mueller et al. | 606/3 |
| 5,435,724 | 7/1995 | Goodman et al. | 433/215 |
| 5,458,594 | 10/1995 | Mueller et al. | 606/3 |
| 5,634,920 | 6/1997 | Hohla | 606/12 |

FOREIGN PATENT DOCUMENTS

| | | |
|---|---|---|
| 0073617 | 3/1983 | European Pat. Off. . |
| 0530574 | 3/1993 | European Pat. Off. . |
| 0619100 | 10/1994 | European Pat. Off. . |
| 3245846 | 7/1983 | Germany . |
| 3415293 | 11/1985 | Germany . |
| 3911871 | 10/1990 | Germany . |
| 4038809 | 4/1992 | Germany . |
| 9201056 U | 7/1993 | Germany . |
| 4211233 | 8/1993 | Germany . |
| 9320739 U | 3/1995 | Germany . |
| 89/11260 | 11/1989 | WIPO . |

*Primary Examiner*—John J. Wilson
*Attorney, Agent, or Firm*—Venable; Robert Kinberg; Catherine M. Voorhees

[57] ABSTRACT

A device for removing material from a workpiece, in particular for removing a hard substance, such as tooth enamel or dentine from a tooth, or for removing ceramic materials, has a laser for irradiating the workpiece in a locally limited ablation area where material is removed, and a handling part (1) which receives the laser or is connected thereto by an optical fiber element or by a mirror arrangement. The handling part (1) is used to position the laser beam (3) in the ablation area and has a distance measurement device (11 to 15, D1, D2) to monitor the depth of material removal. While the material is being removed, the distance measurement device (11 to 15, D1, D2) measures the distance to the workpiece surface in the ablation area and therefore the depth of material removal by means of the material-removing laser or of a measurement beam (11) generated by another laser.

25 Claims, 9 Drawing Sheets

DEVICE FOR REMOVING MATERIAL FROM A WORKPIECE BY LASER RADIATION

BACKGROUND OF THE INVENTION

The invention relates to a device for removing material from a workpiece, particularly removing a hard dental substance such as tooth enamel or dentine from a tooth, or for removing material from ceramic workpieces, by means of a laser.

Devices of this type are known from, for example, DE 41 28 617, GB 01 25 944, U.S. Pat No. 5,020,995, DE 4 038 809, DE 34 15 293 and DE-GM 92 01 056.3, and employ pulsed laser radiation with pulse lengths of either less than 100 ns or greater than 100 μs to remove hard dental substances. The focus size of the laser beam, in other words the expansion of the laser beam on the irradiated workpiece surface, is relatively large, namely between 0.2 and 1.5 mm. It is also known from the cited publications to counteract contamination of the end optics by blasting it free with a water/air spray. It is also known from DE 39 11 871 to use a water/air spray to cool the laser process, which results in a distinct qualitative improvement in the ablation result.

DE 42 11 233 describes a device of this type for removing a hard dental substance, which has an Er:YAG laser that is integrated into a treatment chair and a handle part for positioning the laser beam, with the laser and the handle part being connected by a mirror articulated arm.

In the context of such devices for removing material, it is also known to guide the laser beam line by line over the ablation area (scanning) for attaining uniform material removal.

A disadvantage of the known devices for machining hard dental substances is re-crystallized deposits on the surface of the cavity formed by the radiation. Another problem associated with removing material from teeth is that, as the removal area deepens, the removal rate increases dramatically in the transition from the tooth enamel to the dentine, which may surprise the patient and, in the known devices, can lead to an accidental pulpotomy. A further disadvantage of the known devices is that the relatively high pulse energies give rise to shock waves that may damage the tooth pulp.

SUMMARY OF THE INVENTION

It is therefore the object of the invention to provide a device and a method of the type mentioned at the outset, with which the material removal can be controlled laterally and axially.

The invention includes the technical teaching of using a laser distance-measuring device to continuously measure the distance from the material surface in the ablation region during the material removal in order to determine the depth of the material removal, and, if necessary, to halt or reduce the intensity of the irradiation.

The invention is based on the surprising realization that, with the energy density being maintained, a reduction in the spot diameter—that is, the diameter of the laser beam in the ablation region—and a simultaneous increase in the pulse-repetition rate and a reduction in the pulse energy do not lead to a reduction in the removed quantity in comparison to conventional ablation with high pulse energies. This is surprising because an increase in disturbing edge effects would be anticipated with a reduction in the spot diameter due to the unfavorable ratio of the ablation surface ($\sim r^2$) to the circumference ($\sim r$). The reduction in the spot diameter makes it possible to determine the completed material removal with high local resolution, and—in refining variations of the invention—to control the material removal with high local resolution.

It is therefore also possible to efficiently machine ceramic, biological hard dental substances and plastics with pulse energies of less than 50 mJ and spot diameters of less than 350 μm, taking into consideration the absorption behavior of hard dental substances with wavelengths in a range of 1.9 ... 2.1 μm and 2.5 ... 3.3 μm or 9.2 ... 11 μm, but preferably 2.78 μm and 2.94 μm or 9.6 μm and 10.6 μm, and the use of spray-cooling with a fluid/air mixture. The fluid should have a high absorption for laser energy. The low pulse energies can be compensated through an increase in the pulse rate in a range of 10 Hz ... 10 kHz for attaining a sufficient removal capacity. The following combinations have proven advantageous:

| Spot Diameter (μm) | Energy Density (J/cm$^2$) | Pulse Energy (mJ) | Pulse Rate (Hz) |
|---|---|---|---|
| 150 | 30 | 10 | 500 |
| 240 | 30 | 20 | 250 |
| 350 | 30 | 40 | 125 |
| 540 | 30 | 80 | 62.5 |

Contrary to all current conventional observations, it has been seen that, despite the structural similarity of tooth enamel and dentine, an acceptable compromise between ablation quality and ablation rate can only be found with i different pulse lengths. The pulse lengths for dentine machining are preferably in a range of 100 ... 300 μs, whereas the optimum pulse lengths for machining tooth enamel are in a range of 10 ... 80 μs.

To determine how much material removal has taken place, the invention provides a distance-measuring device, which is disposed in the handle part for guiding the laser beam, and uses a measuring beam to measure the distance from the workpiece to be machined—usually a tooth. The term handle part refers first and foremost to hand-held dental instruments that allow the attending dentist to guide the laser beam in the region of the patient's mouth. However, it also includes devices that are positioned mechanically, for example by robots, which is particularly relevant in the material machining of workpieces in non-medical fields. Here the laser can be selectively disposed directly in the handle part or in a separate device; in the latter case, the handle part and the laser can be connected by light waveguides or a mirror articulated arm, as described in the publications cited at the outset.

The measuring beam serving to measure distance can be generated by a separate laser and coupled coaxially or paraxially into the beam path. Furthermore, it is also possible to use the laser serving in material removal, with a reduced pulse energy, for distance measurement.

In a variation of the invention, the distance measurement is effected through the evaluation of the adaptation of the focal distance between the workpiece surface and the measuring laser. Here the invention utilizes the realization that fanning of the reflected measurement beam is a function of the distance between the focal plane and the workpiece surface. If the surface of the workpiece is exactly in the focal plane, for example, the fanning of the reflected measurement beam is minimal. The fanning of the reflected measurement beam increases with increasing distance between the focal plane and the workpiece surface. Therefore, in this variation, a convergent lens is provided for focusing the measurement beam, the lens being disposed on the machining side in the handle part, in the beam path of the measurement beam. Furthermore, a beam splitter is provided, preferably between the measurement laser and the convergent lens, for coupling out the measurement beam reflected at the workpiece. The beam splitter can comprise a semi-permeable mirror, for example. The reflected measurement beam that is coupled out of the beam splitter is then focussed by a further convergent lens, and evaluated.

The reflected measurement beam can be evaluated, for example, in that a mirror is mounted in the beam path of the reflected measurement beam, the mirror reflecting the reflected measurement beam in its entirety onto a first light detector when the focal plane of the measurement beam and the workpiece surface coincide. As the distance between the focal plane of the measurement laser and the workpiece surface increases, the fanning of the reflected measurement beam increases, so the mirror is irradiated increasingly to the side, and a smaller and smaller proportion of the reflected measurement beam reaches the first light detector. This variation is particularly advantageous in connection with a second light detector that is disposed behind the mirror and detects light that passes the mirror laterally, so high precision can be attained through the formation of the quotient of the intensities measured by the two light detectors.

In another, contrasting variation of the invention, it is provided to couple in the measurement beam serving to measure distance paraxially to the optical axis, so the measurement beam is reflected in the focal point when the focal plane and the workpiece surface coincide, and, with increasing distance between the focal plane and the workpiece surface, the beam travels out to the side. To evaluate the reflected measurement beam, this variation of the invention again includes two light detectors, which are disposed adjacently in the handle part, in the beam path of the reflected measurement beam; when the focal plane and the workpiece surface coincide exactly, the reflected measurement beam virtually exclusively impacts the first light detector, and, as the distance between the focal plane and the workpiece surface increases, the associated lateral travel of the measurement beam also causes it to be increasingly incident at the second light detector, so the distance from the workpiece surface can be calculated from the ratio of the intensities measured by the two light detectors. As in the above-described embodiment, the light detectors can be TGS detectors. Peltier-cooled HgCdTe detectors can be used with wavelengths in a range of 10 $\mu$m, and Peltier-cooled InAs detectors can be used with wavelengths of about 3 $\mu$m.

In the preferred embodiment of the invention, which can be combined with the two above-described variations, the convergent lens provided on the machining side is additionally displaceable in the axial direction, and is moved by an actuating device so as to oscillate in the axial direction. This movement of the convergent lens continuously displaces the focal plane of the measurement beam in the axial direction. The distance from the workpiece surface is calculated by a calculation unit, which is connected on the input side to the actuating device for receiving a signal that represents the respective position of the convergent lens, and to the two light detectors for determining the respective light intensities. The calculation unit evaluates, for example, the phase shift between the lens position and the quotient of the intensities measured by the two light detectors. If the oscillating convergent lens in the above-described embodiment is also passed by the machining laser, the individual pulses of the machining beam should be emitted at the moment when the spot diameter is minimal because of the position of the oscillating convergent lens, which can be achieved by, for example, a triggering of the laser by the output signal of the two light detectors.

In a refining variation of the invention, it is provided to operate the laser serving in material removal only within a certain distance range from the workpiece to be treated—normally a tooth—to preclude, on the one hand, a threat to attending persons by the laser beam, or excessive material removal, and, on the other hand, to prevent excessive irradiation of the workpiece from too close a distance. For this purpose, the calculation unit is connected on the output side to a threshold-value member that compares the distance value determined by the calculation unit to an upper and a lower threshold value and, if the value is exceeded or not met, respectively, the member shuts off the laser.

Through the shut-off of the laser serving in material removal if the predetermined minimum distance from the workpiece is exceeded, as described above, the removal depth can be limited, but the shutoff does not permit the creation of smooth workpiece surfaces. In a refining variation of the invention, therefore, it is provided that the output signal of the calculation unit is supplied to a regulator that automatically adapts the laser power to the distance from the workpiece surface by setting the pulse rate, the pulse length or the pulse energy. As the measured depth approaches the predetermined removal depth, the laser power is correspondingly reduced until the laser is eventually shut off completely once the predetermined removal depth is reached. An advantage of this continuous adaptation of the laser power over the course of the removal process is that very uniform workpiece surfaces can be created, which is particularly crucial in the dental region for preventing the formation of bacterial deposits after hard dental substances have been removed.

In accordance with a further variation of the invention, it is provided to guide the laser beam serving in material removal over the workpiece during the machining, so that larger regions of a workpiece can also be machined with a small spot diameter. For guiding the laser beam, this variation of the invention provides a beam-deflection device, which is disposed in the beam path of the laser beam serving in material removal, and can comprise, for example, a rotatable or pivotable mirror that deflects the laser beam corresponding to the respective mirror position. The mirror can be adjusted, for example, by two stepped motors that rotate the mirror about two axes extending perpendicular to one another, and therefore permit an arbitrary relocation of the ablation region—that is, the spot—on the workpiece surface.

The relocation of the ablation region can be effected, for example, line-wise or column-wise, which is also referred to as raster scanning. It is also possible, however, to deflect the laser beam such that successive ablation points lie as far apart as possible within the area to be machined for permitting an interim cooling of the previously-irradiated ablation region, thus attaining a homogeneous heat distribution. It is also possible, however, to scan circles or ellipses, beginning with a spot diameter of up to 3 mm, as well as lines of up to 3 mm and rectangles with edge lengths of up to 3 mm. With a working distance of 15 mm between the handle part and the workpiece surface, a mirror deflection of about 4° is required, which corresponds to a beam deflection of 8°. In use in the dental region, the guidance of the machining beam is adapted to the desired treatment. Hence, the machining beam is preferably guided over the tooth surface in linear fashion in a fissure treatment. In a caries treatment, in contrast, a circular or elliptical guidance of the machining beam is advisable, whereas guiding the machining beam within a rectangular region is particularly well-suited for preparing retention grooves.

In the preferred embodiment, however, the laser beam is guided over 10 lines with 10 points each by a mirror that is actuated with stepped motors, with 10 ms of time between two points with a 100 Hz pulse rate. If beam blurring of $\frac{1}{10}$ the spot diameter is permitted, 1 ms remains for the laser pulse and depth measurement at 100 Hz, or 100 $\mu$s at 1 kHz.

In contrast, in a further embodiment, a pneumatically- or electrically-driven faceted-mirror scanner is used to deflect the beam. To effect a line scan, the individual mirror facets are tipped toward one another. Because, as a rule, dimensions of only about 15×15 mm are permissible in the head of the handle part, and the beam should not have a diameter of less than 2 mm at the mirror, only a limited number of facets can be realized. One possibility is an octagon with facets that are oriented in the direction perpendicular to the scanner's axis of rotation. If the beam diameter covers $\frac{2}{3}$ of the facets, 15° of the usable scanning angles remain in the octagon. The facet orientation reduces this to the necessary 4–5°.

Two operating modes are possible with these types of scanners:
1. All laser pulses of a scanline are sent to the same facet. With a 100 Hz pulse-repetition rate, the scanner rotates at 96 rpm. Of the total time, however, $\frac{2}{3}$ cannot be used, because with $\frac{2}{3}$ facet coverage a facet edge is located in the beam diameter, which reduces the effective pulse rate to $\frac{1}{3}$.
2. Only one laser pulse is sent to a facet. With 8 facets and a 100 Hz pulse-repetition rate, the scanner rotates at about 750 rpm. The next pulse is offset by one line and one spot diameter. If a beam offset of $\frac{1}{10}$ of the beam diameter is allowed, about 20 $\mu$s are available for the depth measurement and laser pulse.

Acousto-optical or electro-optical deflectors can also be used in addition to the above-described embodiments of the beam-deflection device if scanlines of about 1 mm suffice. Suitable materials for the IR range include Ge or $TeO_2$. The HF actuation power is then about 10 W. It is advantageous to compensate the dropping beam output by correspondingly increasing the pulse energy with an increasing deflection angle.

In a further embodiment of the invention, it is provided to widen the region of the workpiece surface that can be reached by the machining beam by separating the beam deflection into the X and Y directions. In this instance, the machining beam is guided parallel to the object's surface—usually the occlusal surface—and deflected by 900 above the ablation region. The 90° deflection optics thereby partially assumes the task of focusing the laser beam. In the preferred embodiment, a cylindrical lens and a cylindrical concave mirror are used for this purpose. The deflection optics is moved parallel to the beam on two guide rails, with two trapezoidal threaded rods effecting the advancement. As described in detail above, the orthogonal deflection is effected by mechanical, acousto-optical or electro-optical deflectors. In this embodiment, it is advisable to clean ablation products from the deflection mirror and the cylindrical lens by spraying these parts intermittently with an aerosol.

In an advantageous variation of the invention, it is provided to establish a defined position relationship between the handle part and the workpiece to be machined in order to permit material removal in a predetermined geometry. The necessary fixing of the position of the handle part is effected by a holder that receives the handle part and can be secured to the workpiece to be machined. In the use of the handle part in the dental region to remove a hard dental substance, a suitable holder is a rail that can be filled with a molding material and placed onto a row of teeth for fixing the position of the handle part, so the handle part is fixed relative to the respective row of teeth after the molding material has hardened.

An advantage of fixing the handle part relative to the workpiece to be machined is that the skillfulness of the operating personnel has only a small impact on the machining quality, because wobbling of the handle part, for example, is precluded. Furthermore, the fixing of the handle position is a prerequisite for an exact creation of predetermined geometries, which is critical in the preparation of crown stumps and cavities.

In a refining variation of the invention, therefore, it is provided to proceed with computer-controlled material removal after the position of the handle part has been fixed. For this purpose, the handle part is connected to an operation computer that actuates the machining laser and sets the pulse rate, the pulse length and the pulse energy. The operation computer further actuates the beam-deflection device, and can thus guide the machining beam arbitrarily over the workpiece surface, thus creating virtually arbitrary surface geometries. For continuous checking of the surface course, the operation computer receives the output signal of the distance-measuring device. The operation computer can thus predetermine a specific surface course, and machine the workpiece with the machining laser until the workpiece possesses the desired surface shape. The user can select the desired surface shape from a library of standard shapes stored in the operation computer. It is possible, for example, to store surface courses in the operation computer that are necessary later for fixing a crown onto a tooth stump. Retentive patterns can also be created in this way for improving the adhesion of plastic fillings to tooth enamel, for example. Of course, it is also possible to create the desired surface course individually on the operation computer, for example by means of a CAD/CAM system. The user need not predetermine the removal depth for each point of the workpiece surface. It suffices for the user to predetermine the desired removal depth at a few support points, whereupon the operation computer interpolates the removal depth between the support points and actuates the handle part accordingly. In the individual presetting of the desired surface geometry, it is also possible to scan the surface of the workpiece first, and represent it on the screen of the operation computer, for example as a relief image. The user can edit the present surface structure with manually-guided input means, and automatically initiate the machining according to the established changes.

BRIEF DESCRIPTION OF THE DRAWINGS

Other advantageous modifications of the invention are disclosed in the dependent claims and described in detail below by way of the preferred embodiment, with reference to the figures in which:

DETAILED DESCRIPTION OF THE INVENTION

Figure 1:
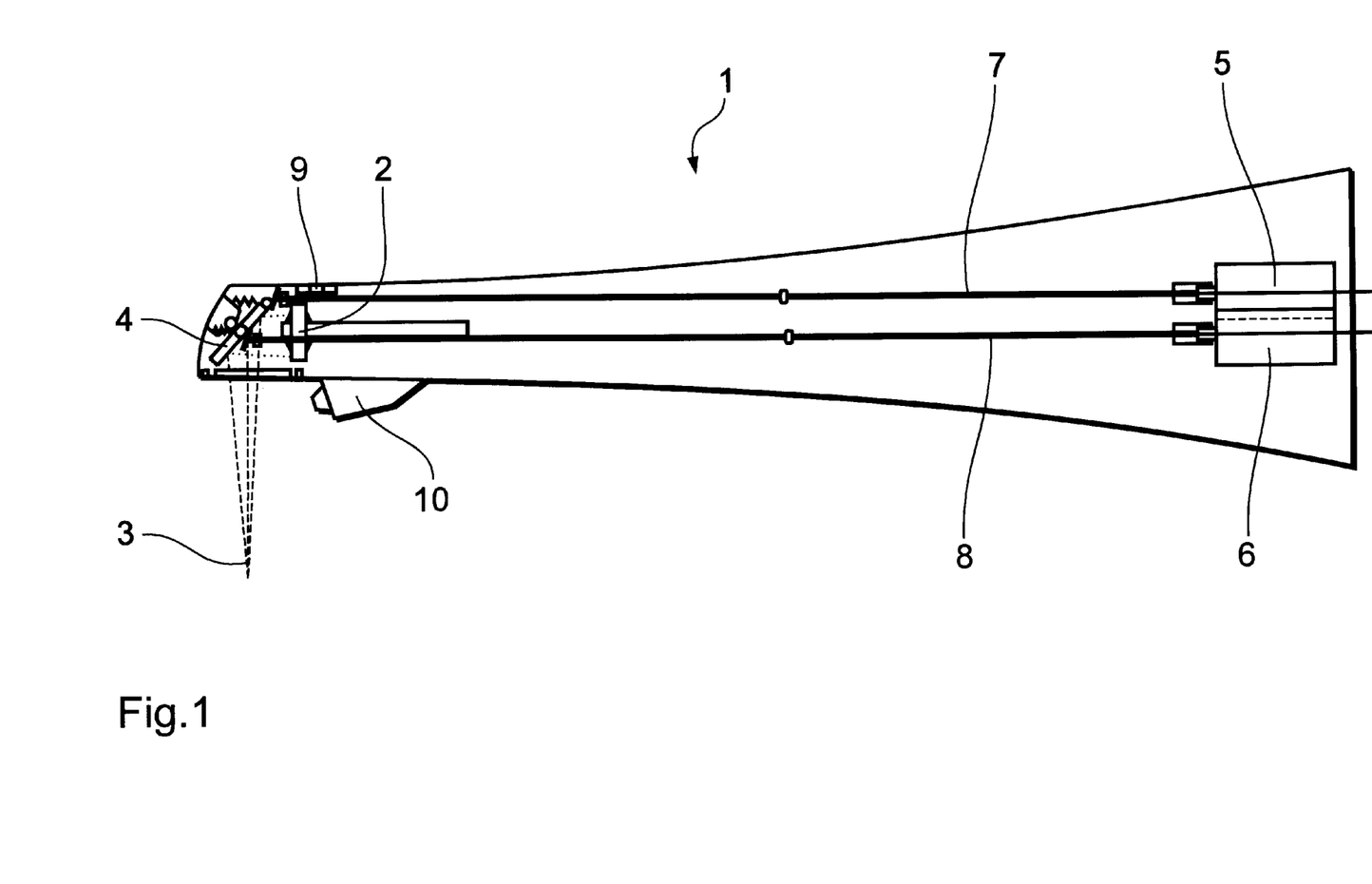
FIG. 1 is as a preferred embodiment of the invention, a handle part for removing a hard dental substance, in a side view.

The handle part 1 of the invention, which is shown in FIG. 1, serves in removing a hard dental substance—such as dentine or tooth enamel—by a dentist. The hard dental substance is removed by a laser beam 3—referred to hereinafter as the machining beam—which is guided to the ablation region via the lens located in a moving-coil system 2, and a deflection mirror 4. An Er:YAG laser having an emission wavelength of 2940 nm serves to generate the machining beam.

To make the impact point of the machining beam 3 on the tooth to be treated visible, despite the fact that the wavelength of the machining beam is not in the visible range, a further laser beam 3—referred to hereinafter as the pilot beam—is additionally provided; this beam is likewise conducted into the ablation region via the deflection mirror 4. At all times, the light point of the pilot beam on the tooth surface allows the attending dentist to know where material is being removed, so he can control the treatment precisely.

Figure 2:
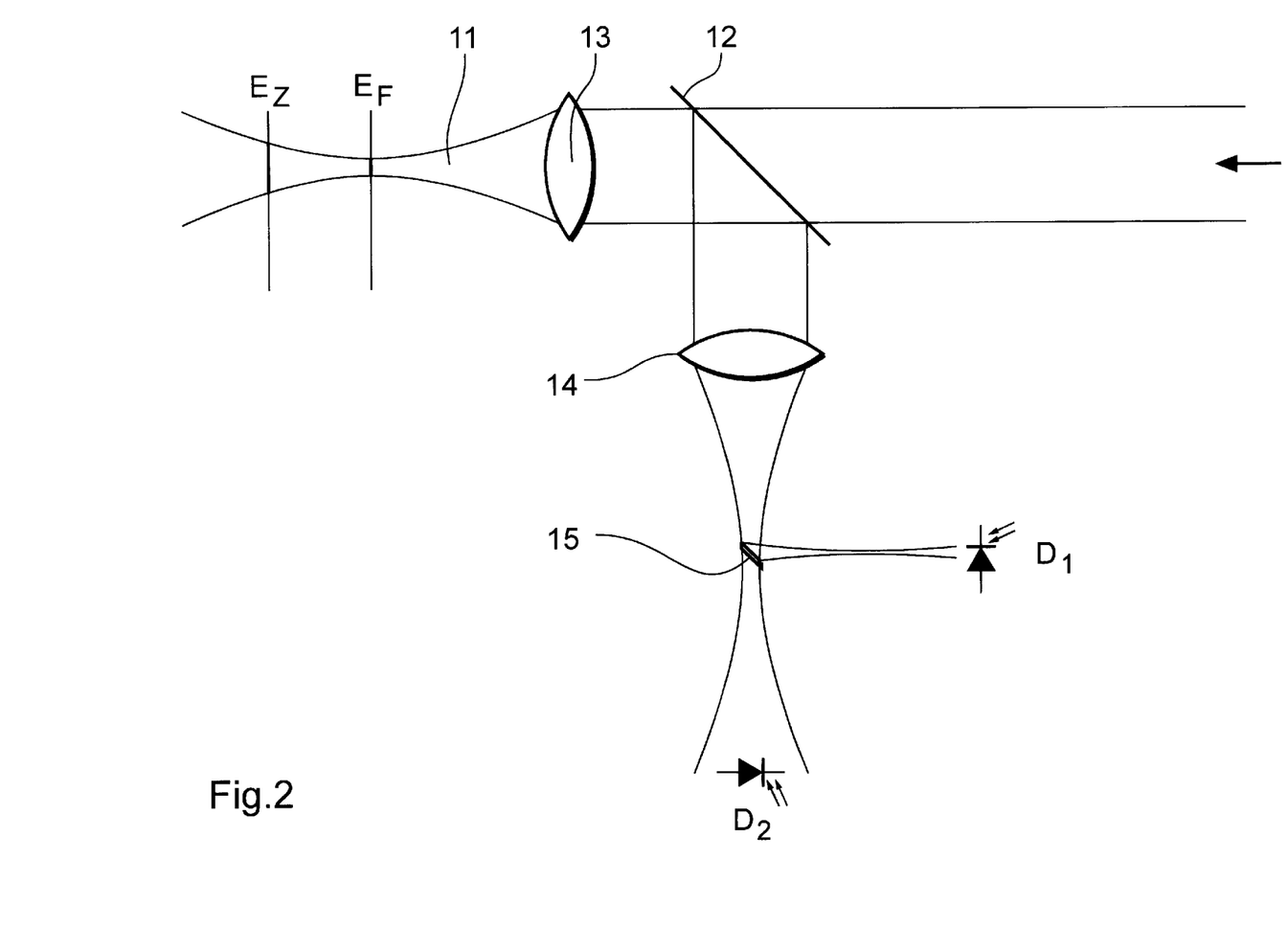
FIG. 2 is a fundamental representation of the distance-measuring device of the device shown in FIG. 1.
Figure 6:
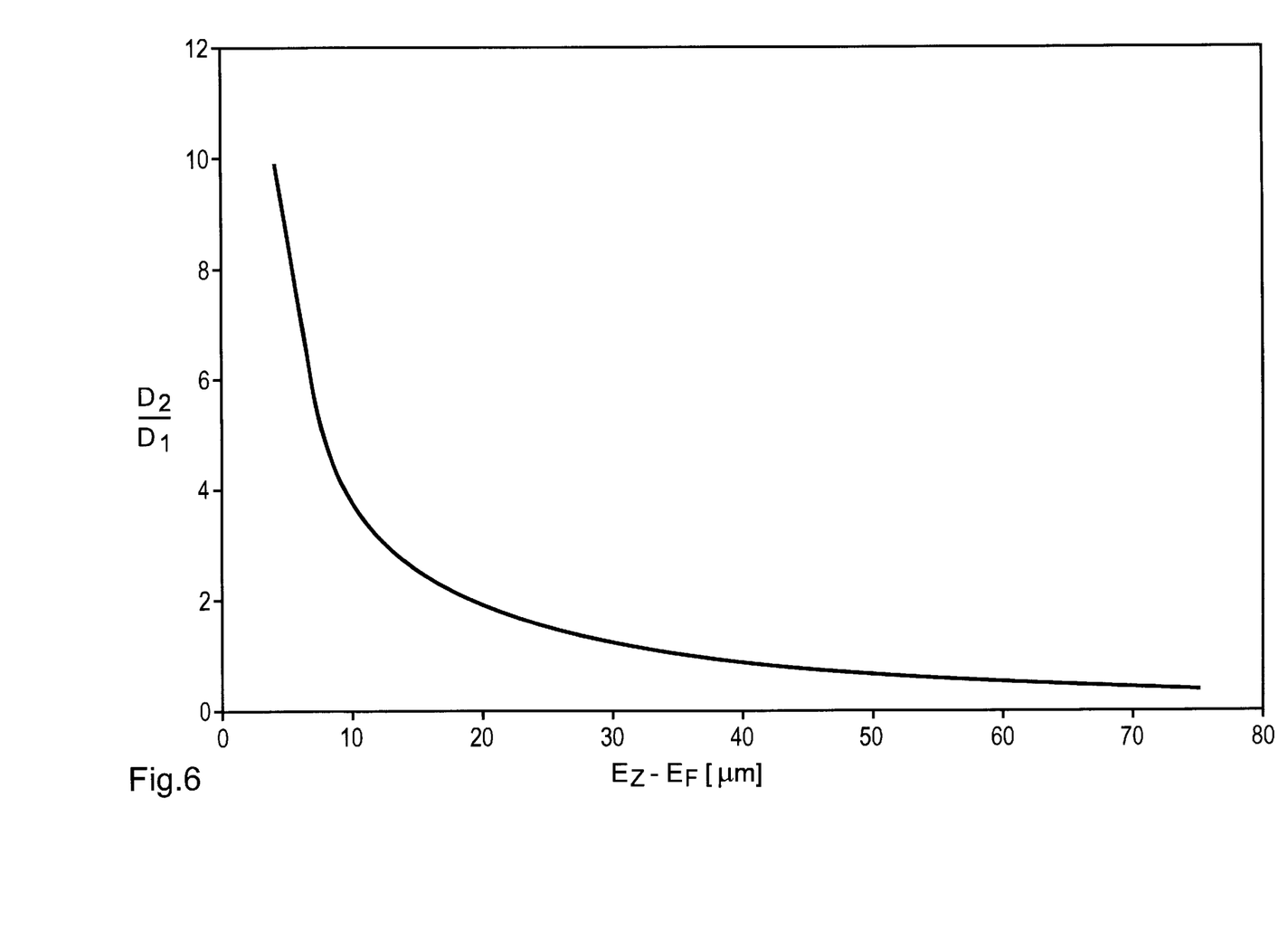
FIG. 6 is a diagram for calculating the distance between the handle part and the tooth to be treated.

The handle part 1 also generates a further laser beam—referred to hereinafter as the measurement beam—that serves in measuring the distance from the ablation region so the depth of the material removal can be controlled. The principle of distance measurement used here is based on the fundamental representation of FIG. 2, which only shows the components that are relevant to distance measurement. The measurement beam 11 passes through the semi-permeable mirror 12 functioning as a beam splitter, and is focussed on the focal plane $E_F$ by the convergent lens 13. The measurement beam 11 reflected at the irradiated tooth is conducted through the convergent lens 13, the beam splitter 12, the convergent lens 14 and the mirror 15 to the light detector $D_1$. The convergent lens 13 continuously performs a paraxial oscillating movement that leads to a corresponding displacement of the focal plane $E_F$. The convergent lens 13 is adjusted electromagnetically by a coil. If the focal plane $E_F$ and the tooth surface $E_Z$ coincide, the spot diameter and the fanning of the reflected measurement beam 11 are minimal, so the mirror 15 guides the reflected measurement beam 11 in its entirety to the light detector $D_1$. In contrast, as the distance between the focal plane $E_F$ and the tooth surface $E_Z$ increases, the spot diameter and thus the fanning of the reflected measurement beam increase, so the beam is increasingly radiated around the mirror 15, and an increasing component of the reflected measurement beam reaches the light detector $D_2$. As can be seen from the diagram in FIG. 6, the formation of the quotient of the $D_1$ and $D_2$ signals results in a pronounced dependency on the distance between the focal plane $E_F$ and the tooth surface $E_Z$, so the distance between the handle part 1 and the tooth surface can be calculated from the phase shift between the quotient $D_1/D_2$ and the coil current that displaces the lens.

Figure 3:
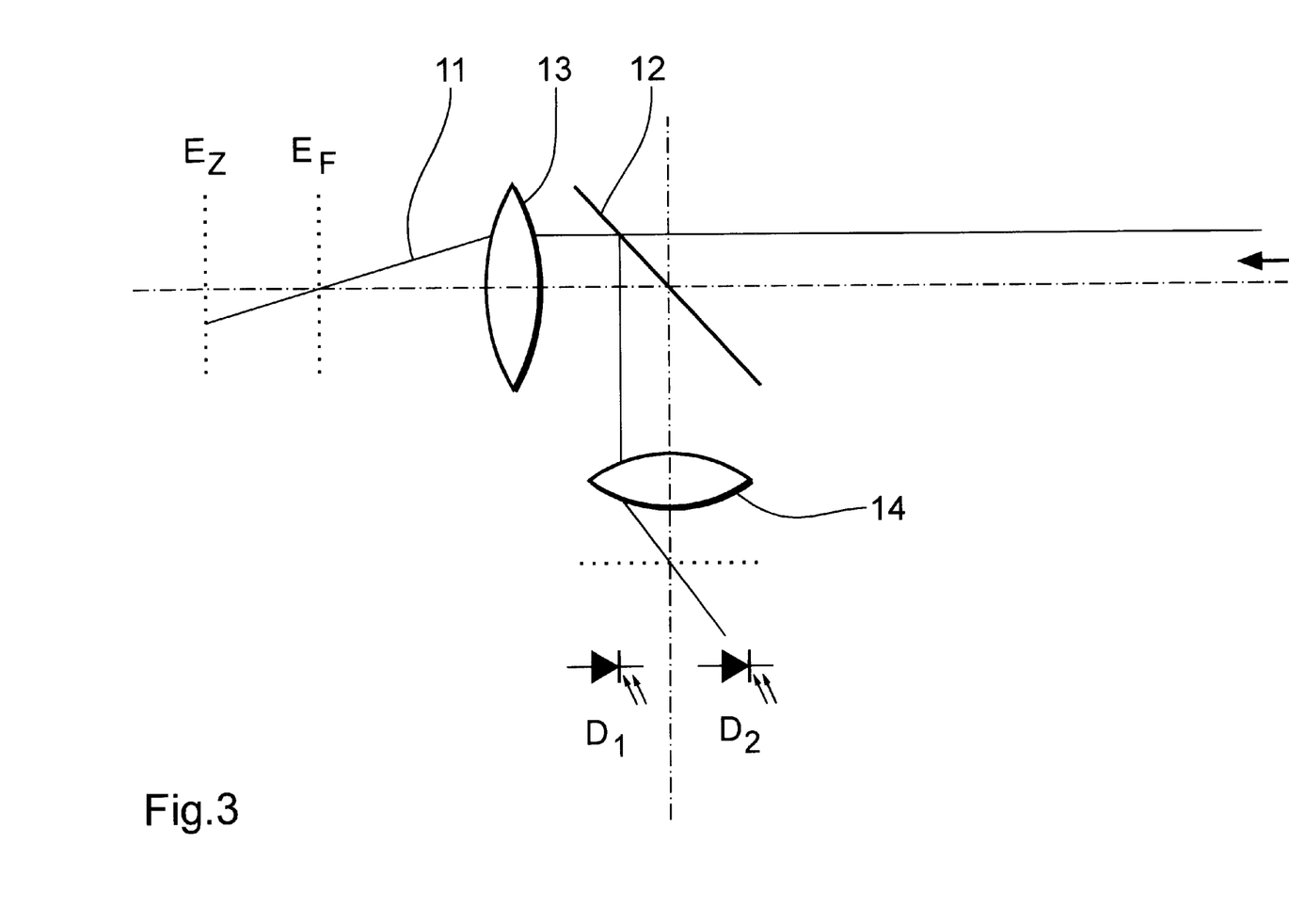
FIG. 3 is a different construction for a distance-measuring device, likewise in a fundamental representation.

FIG. 3 shows an alternative embodiment of a laser distance-measuring device. Because the distance-measuring device illustrated here is largely identical to the distance-measuring device shown in FIG. 2, corresponding components are provided with the same reference characters in the two figures. The measurement beam 11 first extends parallel to and alongside the machining beam, and is conducted into the ablation region by way of the semi-permeable mirror 12 and the convergent lens 13. If the focal plane $E_F$ of the convergent lens and the tooth surface $E_Z$ coincide, the measurement beam 11 impacts the focal point of the convergent lens 13 exactly. In this case, the reflected measurement beam 11 is conducted virtually in its entirety to the light detector $D_1$ by way of the convergent lens 13, the beam splitter 12 and the convergent lens 14. In contrast, as the distance between the focal plane $E_F$ and the tooth surface $E_Z$ increases, the measurement beam 11 travels increasingly to the side, so a correspondingly lower proportion of the reflected measurement beam reaches the light detector $D_1$, changing the difference between the intensities measured by $D_1$ and $D_2$. In this embodiment, the depth information results from the phase shift between the coil current that displaces the convergent lens 13 axially and the difference signal of the two light detectors $D_1$ and $D_2$.

The handle part 1 shown in FIG. 1 also permits the irradiation of a larger region of the tooth surface. To this end, the handle part 1 has a beam-deflection device, which essentially comprises a mirror 4 that can pivot in two directions, by way of which mirror the machining, measurement and pilot beams are guided to the ablation region. The mirror is set by two stepped motors 5, 6, which are connected to two wobble plates by way of a shaft 7, 8, respectively, with the plates deflecting the mirror 4 in a respective direction as a function of the angle of rotation of the shaft 7, 8. The mirror 4 is provided with two helical springs for resetting.

The handle part 1 further includes on its top side, which is visible to the attending dentist, an LED strip 9 that displays the position of the machining point relative to the focal plane, thus permitting the dentist to position the handle part 1.

The handle part 1 also has a metering dispenser 10 that permits a spray to be emitted from the nozzle onto the ablation region for cooling the laser process.

Figure 4:
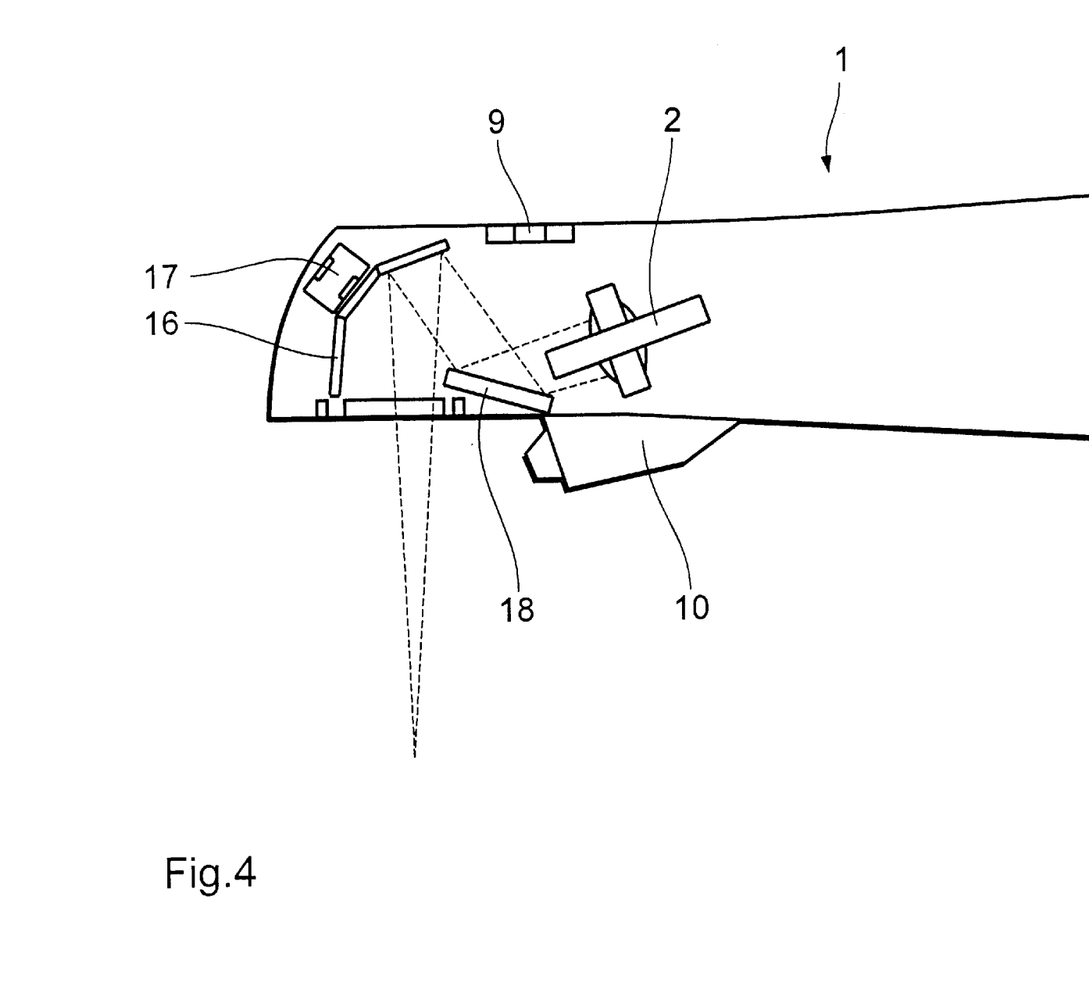
FIG. 4 is the head of the handle part of FIG. 1, with a faceted-mirror scanner for positioning the laser beam.

FIG. 4 shows an alternative embodiment of the beam-deflection device, with only the head of the handle part 1 of the invention being illustrated. For beam deflection, a faceted-mirror scanner 16 is used, which is rotated by a stepped motor 17 and deflects the machining, measurement and pilot beams in different directions as a function of the angle of rotation; the beam deflection can be predetermined by the tipping of the individual mirror facets. To guide the beams, this embodiment includes an additional deflection mirror 18, which conducts the beams emerging from the moving-coil system 2 further to the faceted-mirror scanner 16.

Figure 5:
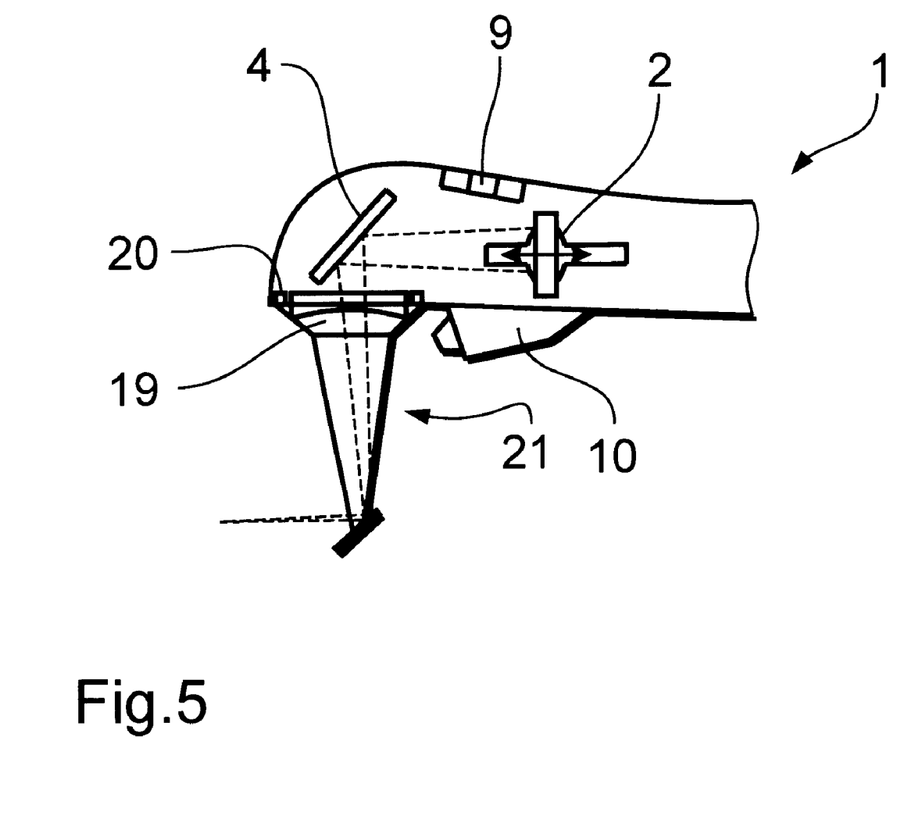
FIG. 5 is the head of the handle part shown in FIG. 4, with an angled extension for deflecting the beam by 90°.

FIG. 5 shows an extension 21, which can be inserted into the annular groove 20 of the handle part 1, for a 90° beam deflection. Through the 90° beam deflection, the extension 21 permits the machining of the walls of the approximal box in a tooth treatment involving Class II cavities. Because the extension 21 increases the distance from the focal plane, a concave lens 19 is provided for widening the beam.

Figure 7:
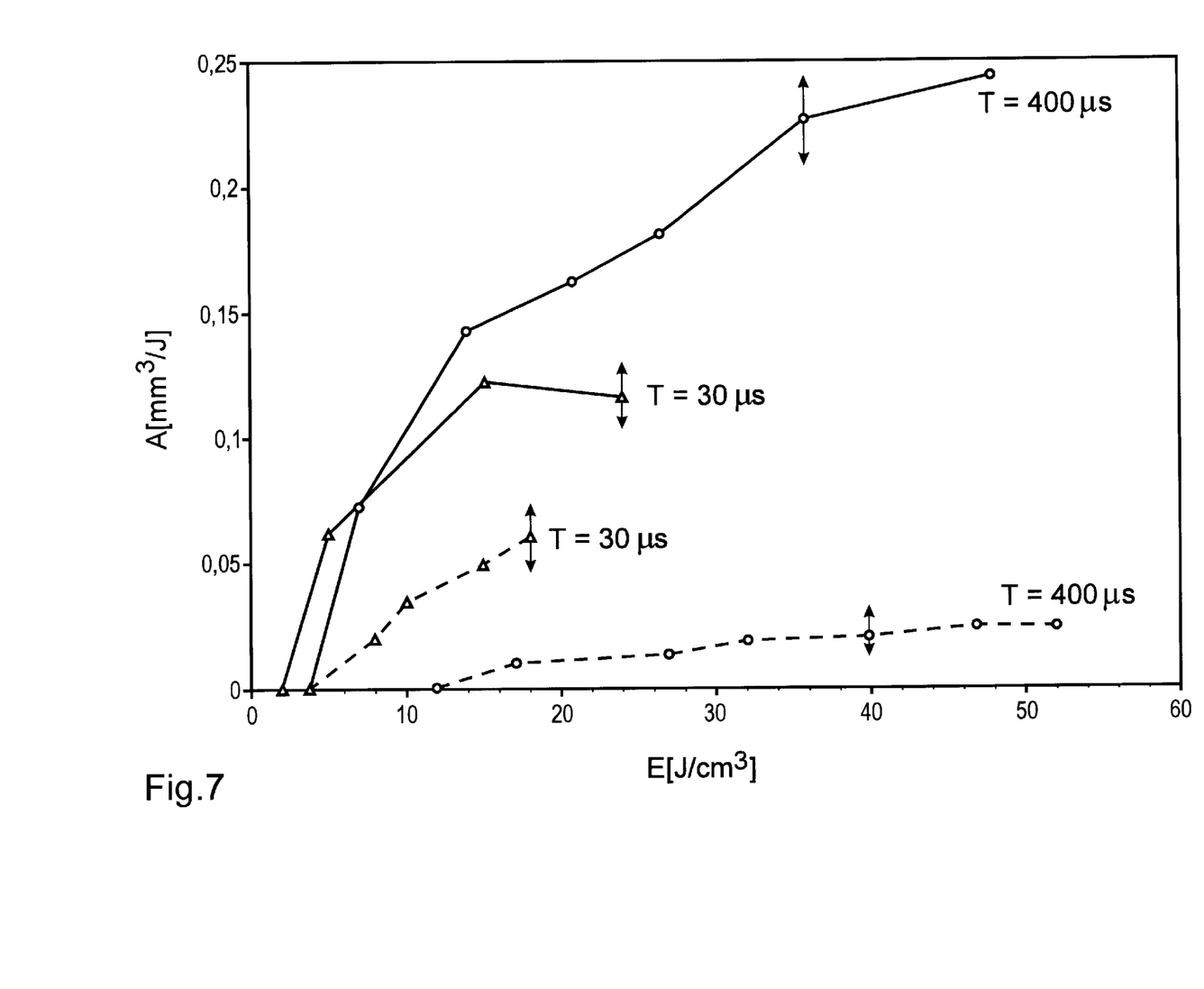
FIG. 7 illustrates the dependency of the removed quantity on the energy density for dentine and tooth enamel, with the pulse length as a parameter.

Finally, FIG. 7 shows the dependency of the removed quantity A on the energy density of the laser irradiation for tooth enamel and dentine, with the pulse length as a parameter. The solid lines indicate the course of the removed quantity for dentine, while the dashed lines show the same dependency for tooth enamel. From the comparison of the two curves, it is apparent that the removed quantity of dentine is significantly larger than that of tooth enamel, which, in uncontrolled hard dental substance removal, leads to a sudden increase in the removed quantity in the transition from tooth enamel to dentine, and can cause an accidental pulpotomy. Furthermore, the diagram indicates that the removed quantity A definitely does not decrease, and usually even increases, when the pulse length T decreases and the energy density E remains the same.

Figure 8:
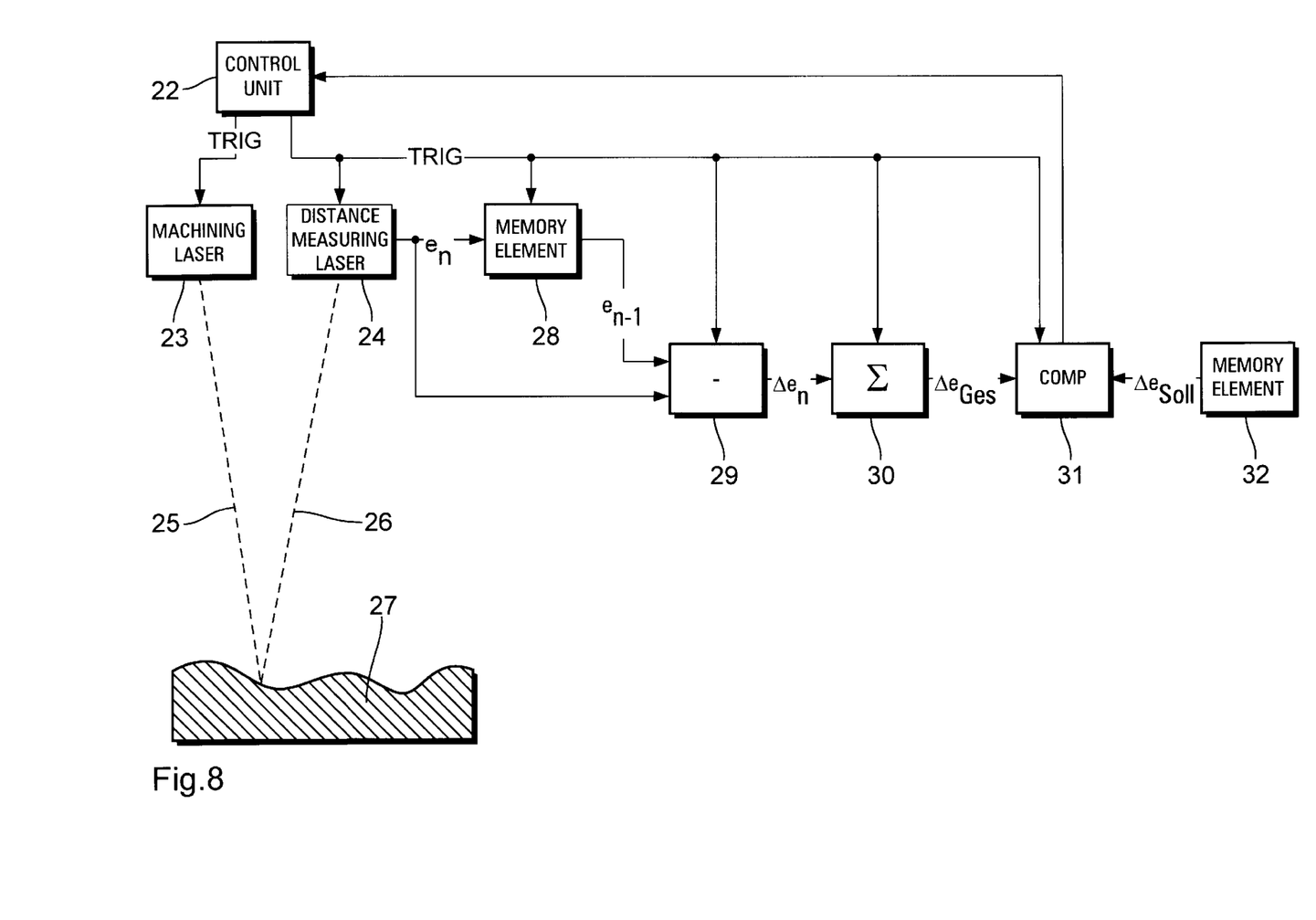
FIG. 8 is a circuit for calculating the removal depth from the measured distance and for depth control of the material removal.

The circuit shown in FIG. 8 serves in calculating the material-removal depth from the distance between the handle part and the surface of the workpiece 27 in the ablation region, the distance having been determined by the distance-measuring device 24. The laser 23 serving in material removal and the laser 24 for measuring distance are controlled by the control unit 22, which transmits trigger pulses, at certain time intervals, to the laser 23 serving in material removal, whereupon the machining beam 25 impacts the workpiece surface in pulses. Following each pulse, the distance-measuring device 24 is actuated by a trigger pulse, and then measures the distance between the handle and the workpiece surface with the measurement beam 26, as described at the outset. The distance $e_n$ determined by the distance-measuring device 24 is then supplied to the memory element 28 and stored temporarily. Following completion of the measurement process, the control unit 22 again transmits a trigger pulse to the machining laser 23, which again generates a pulse for material removal. The distance-measuring device 24 is subsequently actuated again, and 2 measures the current distance $e_n$ and transmits it from the output side to both the memory element 28 and the subtracter 29. The subtracter 29 uses the distance $e_{n-1}$ and the current distance $e_n$, which were measured prior to the last pulse and are stored in the memory element 28, to calculate the material-removal depth effected by the previous pulse. This value $\Delta e_n$ is then supplied to the calculation unit 30, which calculates the sum $\Delta e_{Ges}$ of the material-removal depths $\Delta e_n$ over a plurality of successive pulses. The total removal depth $\Delta e_{Ges}$, which results from a pulse sequence up to the last pulse, therefore appears at the output of the calculation unit 30. The comparator unit 31 then compares this value $\Delta e_{Ges}$ to the desired removal depth $\Delta e_{SOLL}$, which is stored in the memory element 32 and can be predetermined by the user. On the output side, the comparator unit 31 is connected to the control unit 22, which continues the material removal with the laser 23 until the attained removal depth $\Delta e_{Ges}$ is less than the desired removal depth $\Delta e_{SOLL}$.

Figure 9:
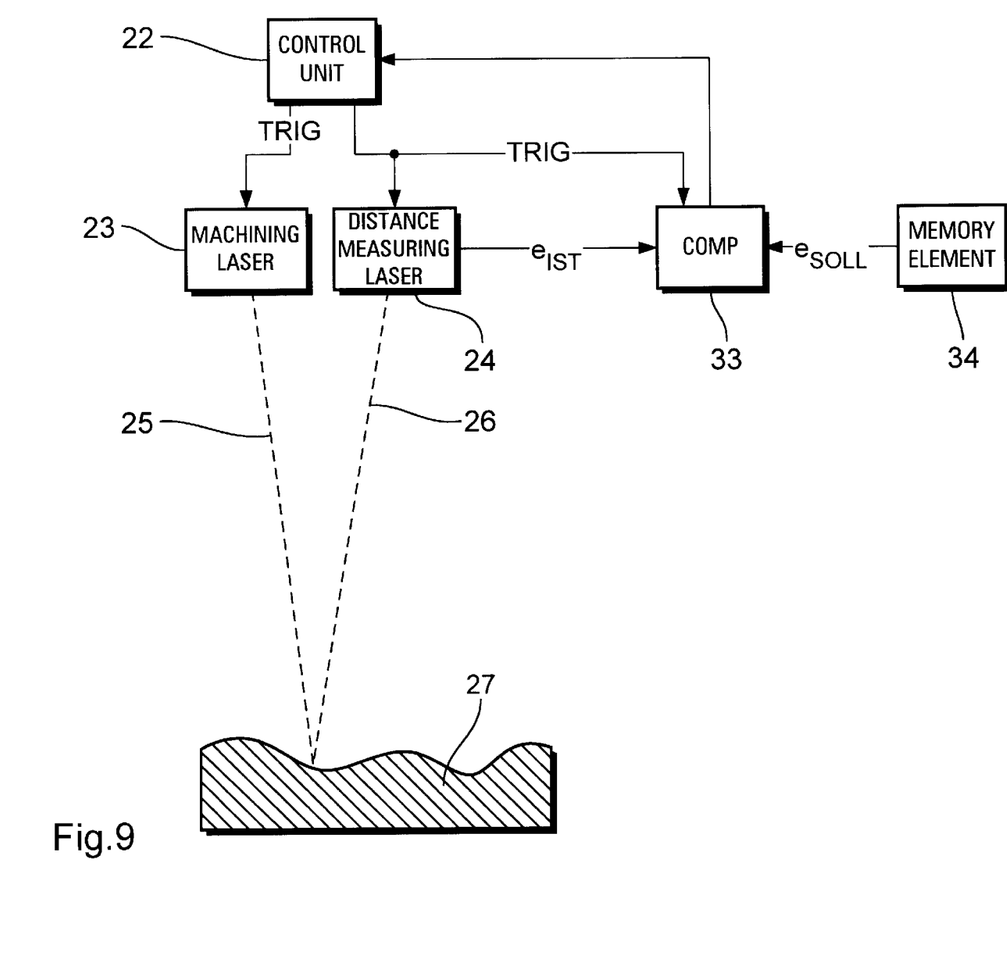
FIG. 9 is a circuit for limiting the removal distance to a predetermined maximum value.

The circuit shown in FIG. 9 likewise serves in controlling the material removal. Unlike in the circuit shown in FIG. 8, however, it is not the removal depth that is not limited, but the machining distance. The laser 23 therefore removes material from the workpiece 27 until a predetermined maximum distance $e_{SOLL}$ has been attained between the handle part and the workpiece surface. For this purpose, the distance-measuring device 24 is connected on the output side to the comparator unit 33, which, following each pulse of the machining beam 25, compares the current measured distance $e_{IST}$ between the handle and the workpiece surface to the maximum machining distance $e_{SOLL}$, which is stored in the memory element 34 and can be predetermined by the user.

The invention is not limited in its embodiment to the above-disclosed, preferred embodiments. Rather, a number of variations are conceivable that make use of the illustrated solution, even in fundamentally different embodiments.

We claim:

1. A device for removing material from a workpiece comprising:
    a laser for irradiating the workpiece in a locally-limited ablation region for removing material; and
    a handle part that receives the laser, for positioning a laser beam in the ablation region, wherein the handle part has a distance-measuring device for controlling the depth of the material removal, the distance-measuring device employing the laser that serves in material removal to generate a measurement beam for measuring the distance between the workpiece surface in the ablation region and a reference point during the material removal, the reference point being in a fixed position relationship relative to the handle part.

2. The device according to claim 1, wherein the material removing device removes at least one of a hard dental substance including tooth enamel and dentine from a tooth, and material from ceramic workpieces.

3. The device according to claim 1, wherein the handle part is connected to the laser by way of one of a light-guide element and a mirror arrangement.

4. The device according to claim 1, further comprising a subtracter for calculating the removal depth ($\Delta e_{Ges}$) from the distance ($e_n$) determined by the distance-measuring device, the subtracter being connected on the input side to the distance-measuring device for receiving the current distance ($e_n$), and to a memory element for receiving a distance value ($e_{n-1}$) that defines the distance of a reference plane from the workpiece surface.

5. The device according to claim 4, further comprising a comparator unit connected to the subtracter for receiving the current removal depth ($\Delta e_{Ges}$) and to a memory element that contains a desired removal depth ($\Delta e_{SOLL}$), the comparator unit being connected on the output side to one of the laser for actuation and an output unit for representing the result of the comparison.

6. The device according to claim 1, further comprising a comparator unit connected to the distance-measuring device for receiving the current measured distance ($e_{IST}$), and to a memory element that contains a desired removal depth ($\Delta e_{SOLL}$), the comparator unit being connected on the output side to one of the laser for actuation and an output unit for representing the result of the comparison.

7. The device according to claim 1, wherein the distance-measuring device has a first convergent lens for focusing the measurement beam in the ablation region; a first beam splitter for coupling out the measurement beam reflected in the ablation region, the splitter being disposed in the path of the measurement beam; a second convergent lens for bundling the measurement beam reflected at the first beam splitter; and two light detectors for determining the distance from the workpiece surface in the ablation region, the detectors being disposed with spacing on the side of the second convergent lens that faces away from the first beam splitter in the path of the measurement beam reflected in the ablation region in order to detect the measurement beam, the detectors further being connected on the output side to a calculation unit for calculating the distance from the workpiece surface in the ablation region as a function of the output signals of the two light detectors.

8. The device according to claim 7, wherein the measurement beam and the laser beam serving in material removal extend essentially coaxially, and further comprising a second beam splitter on the side of the second convergent lens that faces away from the first beam splitter, the second beam splitter splitting essentially coaxial measurement eam and laser beam into partial beams, the two light detectors being disposed in the respective beam path of one of the partial beams exiting the second beam splitter.

9. The device according to claim 7, wherein the measurement beam and the laser beam extend paraxially between the first convergent lens and the ablation region, and the two light detectors are disposed adjacently, with respect to their optical axis, on the side of the second convergent lens that faces away from the first beam splitter.

10. The device according to claim 7, wherein the first convergent lens is disposed to be displaced paraxially, and further comprising a first actuating device for displacing the lens paraxially and with an oscillating movement, the actuating device being connected on the output side to the calculation unit for emitting a signal that represents the position of the first convergent lens, and for calculating the distance from the workpiece surface from the output signals of the two light detectors and the position signal of the first convergent lens.

11. The device according to claim 7, wherein the calculation unit is connected on the output side to a threshold-value member for shutting off the laser if the distance from the workpiece surface is one of less than a predetermined minimum distance, and greater than a predetermined maximum distance.

12. The device according to claim 7, wherein the calculation unit is connected on the output side to a regulator for regulating the laser as a function of the measured distance from the workpiece surface.

13. The device according to claim 7, wherein the calculation unit is connected on the output side to a display for a visual representation of the distance from the workpiece surface.

14. The device according to claim 1, further comprising a holder for fixing the position of the handle part relative to the workpiece to be machined during the material removal.

15. The device according to claim 14, wherein the holder has a rail that can be filled with molding material and whose course can be adapted to a row of teeth for fixing the handle part to a portion of the row of teeth.

16. The device according to claim 1, further comprising a beam-deflection device for relocating the ablation region on the workpiece surface, the beam-deflection device being disposed in the beam path of the laser beam serving in material removal, and adjustable with respect to the beam direction.

17. The device according to claim 16, wherein the beam-deflection device comprises a pivotable mirror that is disposed in the beam path of the laser beam serving in material removal.

18. The device according to claim 16, wherein the beam-deflection device comprises a mirror facet (16) that is disposed in the beam path of the laser beam serving in material removal, the mirror facet being one of rotatable or pivotable.

19. The device according to claim 16, further comprising a second actuating device for adjusting the beam-deflection device.

20. The device according to claim 19, wherein the distance-measuring device and the second actuating device serving in adjusting the beam-deflection device are connected to an operation computer for computer-controlled material removal.

21. The device according to claim 1, further comprising a second laser for generating the measurement beam, the emission wavelength of the second laser essentially lies in the absorption maximum of the workpiece material for avoiding interfering optical scatter in the ablation region.

22. The device according to claim 1, wherein the laser for material removal is one of a CTE laser having a wavelength of 2.69 $\mu$m, an Er:YSGG laser having a wavelength of 2.78 $\mu$m, an Er:YAG laser having a wavelength of 2.94 $\mu$m, and a $CO_2$ laser having a wavelength of 9.6 $\mu$m or 10.6 $\mu$m.

23. The device according to claim 1, wherein the laser is a pulsed laser having a pulse length between 1 $\mu$s and 100 $\mu$s and a pulse rate between 10 Hz and 100 kHz.

24. The device according to claim 1, further comprising a fluid dispenser for cooling the workpiece surface in the ablation region and its surrounding field, the fluid being dispensed by the fluid dispenser having its maximum absorption in the range of the wavelength of the laser beam serving in material removal.

25. The device according to claim 1, wherein a target laser is provided for illuminating the ablation region, the emission wavelength of the target laser being in the visible wavelength range.

* * * * *